United States Patent [19]

Klehm

[11] Plant 4,248

[45] May 2, 1978

[54] PEONY NAMED CHEDDAR GOLD

[75] Inventor: Roy G. Klehm, Barrington, Ill.

[73] Assignee: Klehm Boys Partnership, Arlington Heights, Ill.

[21] Appl. No.: 795,311

[22] Filed: May 9, 1977

[51] Int. Cl.[2] ..... A01H 5/00
[52] U.S. Cl. ..... Plt./68
[58] Field of Search ..... Plt./68

*Primary Examiner*—Robert E. Bagwill
*Attorney, Agent, or Firm*—Charles W. Rummler

[57] ABSTRACT

A new variety of peony *lactiflora* distinguished by a profuse production of medium sized flowers with petalage of the Japanese type providing large, white, rounded, and smooth guard petals surrounding a large central mass of yellow stamenoids, the flowers being further distinguished by the unusual appearance of white petaloids at the center of the bloom and by a high degree of peony fragrance. This plant is of medium height with average strength, a rapid growth rate and abundant clear green foliage, and a mid-season blooming habit.

1 Drawing Figure

BACKGROUND OF THE NEW PLANT

My new variety of peony plant is a seedling of Charlies White (U.S. Plant Pat. No. 3,684) × Bowl of Cream (U.S. Plant Pat. No. 2,451) resulting from a cross made during the course of breeding efforts carried on by members of my family in our nursery at Arlington Heights, Ill., with the object of developing new peony varieties having strong, stiff, weather resistant stems and blooms of pleasing colors and color combinations.

This new plant was observed by me to have interesting and unusual blossom characteristics, quite different than those of its parents, and my propagation of this plant by root division, through successive generations at Arlington Heights, Ill., has demonstrated that its distinctive characteristics hold true from generation to generation and appear to be firmly fixed. Commercial scale propagation of this new peony plant is now being carried on at production grounds at Champaign, Ill., and at Arlington Heights, Ill.

DESCRIPTION OF THE DRAWING

This new variety of peony plant is illustrated by the accompanying photographic drawing which, in full color, shows two face views of the flower. The left hand view shows the newly opened bloom and the right hand view shows the form and petalage character of the mature, fully opened flower. The colors shown are as nearly true as it is reasonably possible to obtain by conventional photographic procedures.

DESCRIPTION OF THE NEW PLANT

The following is a detailed description of my new peony plant variety with the color designations being according to the R.H.S. Colour Chart published by The Royal Horticultural Society of London, England, with collaboration of The British Colour Council, the observations having been made at Arlington Heights, Ill., during the flowering season of 1976.

THE PLANT

Origin: Seedling.
Parentage:
*Seed parent.*—Charlies White (U.S. Plant Pat. No. 3,684).

*Pollen parent.*—Bowl of Cream (U.S. Plant Pat. No. 2,451).
Classification: *Paeonia lactiflora.*
Form: Round, multistemmed bush.
Growth: Rapid and vigorous with average strength and sturdiness.
*Branching.*—None.
*Cane size.*—About 1⅛ inches in diameter.
Foliage: Quantity — abundant with numerous leaves.
*Leaf size.*—Large.
*Leaf shape.*—Elliptically acute with smooth margins.
*Aspect.*—Smooth and glossy.
*Color.*—Upper side — Forest Green, RHS 135A. Under side — Almond Green, RHS 135B.

THE BUD

Size: Medium.
Form: Globular and smooth — slightly ovoid.
*Diameter.*—About 1⅛ inches.
*Depth.*—About 1¼ inches.
Opening rate: Average.
Color of bud: When sepals first divide — RHS 158D.
Sepals: Hooded over bud until dividing.
*Color.*—Inside — Limpid Green, RHS 135D. Outside — Medium Green, RHS 135C.
Calyx: Shape — Polysepalous.
*Size.*—Average.
*Aspect.*—Glandular.
*Splitting.*—Calyx does not split.

THE FLOWER

Blooming habit: This plant is a midseason bloomer, blooming profusely once each year in the spring.
Borne: Singly, with two to four axillary buds on each stem.
Size: Medium.
*Diameter.*—6½ to 7 inches.
Shape: Cup-shaped when bloom first opens, the petals surrounding a large mass of staminodes and spreading outwardly as the bloom matures.
Petalage: Number of petals — 12 to 16.
*Arrangement.*—Imbricated.
*Form.*—Japanese type with relatively smooth margins.

*Color.*—All petals, upper side — Cream White, RHS 158D. Reverse side — RHS 158C.

*Texture.*—Soft.

*Appearance.*—Shiny and satiny.

Petaloids: Several, appearing at the center of the massed staminodes.

*Color.*—White, RHS 158D.

Fragrance: A high degree of peony fragrance.

Effect of weather: The flower is not abnormally affected by weather.

Persistence: Petals drop off the stem for complete dehiscence.

Disease resistance: This plant resists leaf blotch and botrytis as observed at Champaign, Ill., and Arlington Heights, Ill.

Lasting quality:

*On plant.*—About 10 days.

*As a cut flower.*—8 to 9 days.

REPRODUCTIVE ORGANS

Staminodes: Numerous in number, closely grouped in a central mass of about $\frac{1}{3}$ to $\frac{1}{2}$ the diameter of the blossom.

*Length.*—$1\frac{1}{2}$ to $1\frac{3}{4}$ inches.

*Pollen.*—Color — Aureolin, RHS 12A.

Pistils: Number — 2 or 3.

*Styles.*—$\frac{1}{2}$ to $\frac{5}{8}$ inch long.

The fruit of this plant is infertile.

This plant, in many respects, has characteristics like those of its seed parent, Charlies White (U.S. Plant Pat. No. 3,684), and its flower resembles that of Lotus Queen (unpatented). The most distinctive feature of this plant, however, is the flower which exhibits large, white and rounded guard petals which surround a most pleasing central mass of yellow staminodes at the very center of which unusual white petaloids generally appear. This blossom coloration, in combination with the clean green foliage, provides a most pleasing garden subject.

I claim:

1. A new and distinct variety of peony *lactiflora* substantially as herein shown and described, characterized by its profuse production of medium sized white flowers having spreading Japanese style, rounded guard petals which surround a large mass of yellow staminodes, at the center of which white petaloids generally appear.

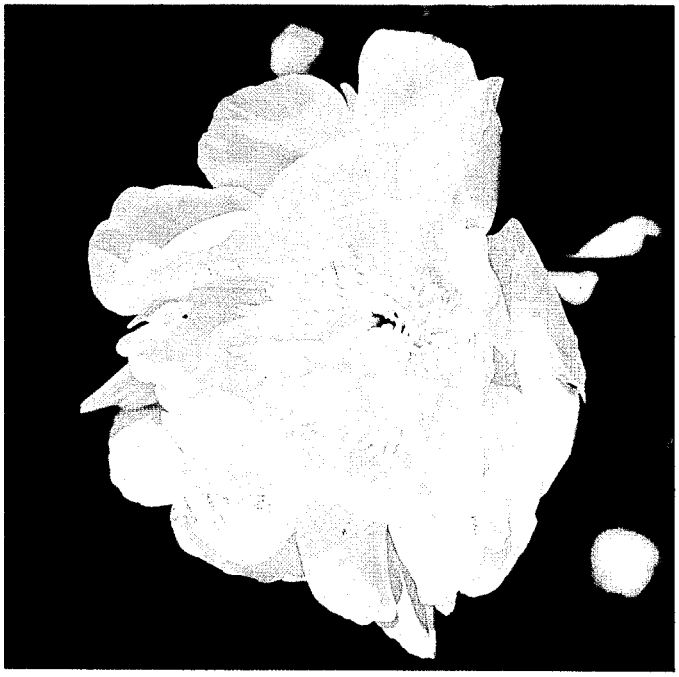
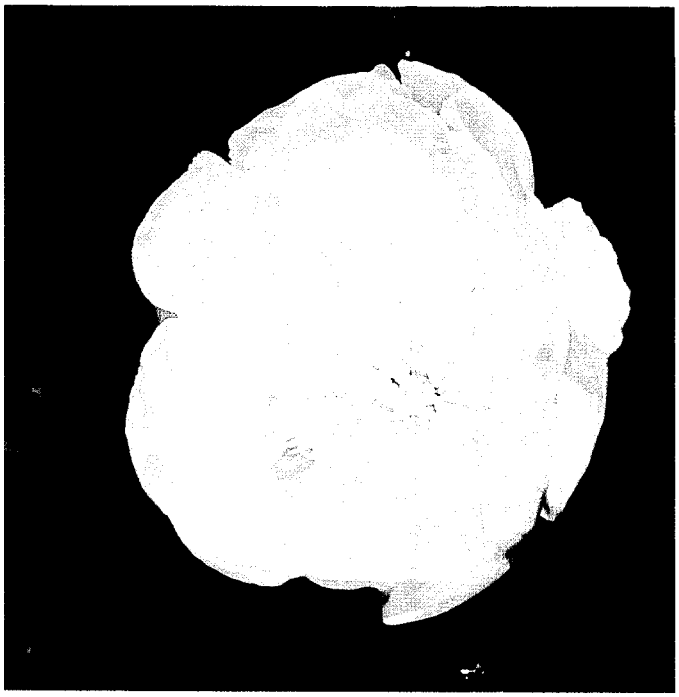

* * * * *